United States Patent [19]
Mikhail

[11] Patent Number: 5,489,310
[45] Date of Patent: Feb. 6, 1996

[54] UNIVERSAL GLENOID SHOULDER PROSTHESIS AND METHOD FOR IMPLANTING

[76] Inventor: W. E. Michael Mikhail, 4203 Shamley Green, Toledo, Ohio 43623

[21] Appl. No.: 267,064

[22] Filed: Jun. 27, 1994

[51] Int. Cl.$^6$ .................................. A61F 2/40; A61F 2/30
[52] U.S. Cl. ................................. 623/19; 623/18
[58] Field of Search ........................ 623/18–21; 606/67, 606/80, 83, 85, 95, 96, 100, 102, 104

[56] References Cited

U.S. PATENT DOCUMENTS

| | | |
|---|---|---|
| D. 285,969 | 9/1986 | Kinnett . |
| D. 295,076 | 4/1988 | Homsy et al. . |
| 3,916,451 | 11/1975 | Buechel et al. ............ 623/18 |
| 3,979,778 | 9/1976 | Stroot ........................ 3/1.91 |
| 4,045,826 | 9/1977 | Stroot ........................ 3/1.91 |
| 4,167,047 | 9/1979 | Grundei et al. ............ 623/20 |
| 4,261,062 | 4/1981 | Amstutz et al. ............ 623/19 |
| 4,502,161 | 3/1985 | Wall ........................... 623/18 |
| 4,550,450 | 11/1985 | Kinnett . |
| 4,625,722 | 12/1986 | Murray ...................... 606/95 |
| 4,693,723 | 9/1987 | Gabard . |
| 4,822,366 | 4/1989 | Bolesky ..................... 623/20 |
| 4,865,605 | 9/1989 | Dines et al. . |
| 4,919,669 | 4/1990 | Lannelongue . |
| 4,964,865 | 10/1990 | Burkhead et al. . |
| 4,979,957 | 12/1990 | Hodorek ..................... 623/20 |
| 4,986,833 | 1/1991 | Worland . |
| 5,030,219 | 7/1991 | Matsen, III et al. . |
| 5,032,132 | 7/1991 | Matsen, III et al. ....... 623/19 |
| 5,080,673 | 1/1992 | Burkhead et al. . |
| 5,197,986 | 3/1993 | Mikhail ...................... 623/20 |
| 5,236,462 | 8/1993 | Mikhail ...................... 623/20 |
| 5,282,865 | 1/1994 | Dong . |
| 5,383,937 | 1/1995 | Mikhail ...................... 623/20 |

FOREIGN PATENT DOCUMENTS

| | | | |
|---|---|---|---|
| 2652498 | 4/1991 | France | 623/9 |

OTHER PUBLICATIONS

Orthomet Brochure, copyright 1993 Orthomet, Inc. 6301 Cecilia Circle, Minneapolis, MN 55439–2713, entitled "Orthomet: Now the Exclusive U.S. Distributor of the 3M™ Neer II and Modular Shoulder Systems".

Brochure entitled "Fenlin Total Shoulder Surgical Technique" copyright 1988, 1989, 1991, Zimmer Inc.

Brochure entitled "Fenlin Total Shoulder" copyright 1993, Zimmer, Inc.

*Primary Examiner*—David Isabella
*Assistant Examiner*—Laura Fossum
*Attorney, Agent, or Firm*—Emch, Schaffer, Schaub & Porcello, Co.

[57] ABSTRACT

A glenoid component for a shoulder prosthesis includes a body having a concave lateral articulating surface and an opposing medial surface with a stem extending along a central axis from said medial surface. The medial surface includes a central portion extending outwardly from the central axis and tapering toward said lateral articulating surface from an area of greater thickness of said body in the vicinity of said central axis to an area of lesser thickness outwardly from said central axis. Under one embodiment the body portion has an edge having a generally circular configuration while under a second embodiment the body portion includes an edge having a non-circular configuration and the tapering central portion terminates in a circular line of termination which is spaced from said edge in one or more areas and cooperates with said edge to define one or more extension portions. A method for and apparatus for use in implanting the glenoid component includes a combination sizer and guide and a reamer having a tapered cutting edge extending from a head in which a peripheral edge portion is contoured to engage the glenoid surface to prevent reaming to an excessive depth.

15 Claims, 8 Drawing Sheets

UNIVERSAL GLENOID SHOULDER PROSTHESIS AND METHOD FOR IMPLANTING

BACKGROUND ART

The present invention relates to a universal glenoid component for a shoulder prosthesis and to a method for implanting such component which will minimize the amount of bone structure required to be removed from the scapula.

In the implantation of a glenoid prosthesis in a scapula, it is desirable that as little of the bone material forming the neck of the scapula as possible be removed when the scapula is prepared to receive the glenoid component. In preparing the scapula to receive a glenoid component, a cavity is formed primarily in the neck of the scapula in which the glenoid component may be positioned, either directly in the cavity if the glenoid component is of the type intended for use without bone cement or implanted in bone cement if the glenoid component is of the type intended to be held in place by bone cement. In either event, it is desirable to remove as little bone structure from the scapula as possible in preparing the scapula to receive the glenoid component.

Prior art shoulder replacement prosthesis disclose many different procedures and different shapes of glenoid components of total shoulder prostheses which require removal of extensive amounts of bone from the scapula in preparing it to receive a glenoid component.

For example, U.S. Pat. No. 4,550,450 (incorporated herein by reference) discloses a total shoulder prosthesis system having a glenoid component 12 with a fixation keel 27 projecting rearwardly from base member 26 for fixation into the cancellous component of the scapular neck. The fixation keel 27 along with the enlarged surface of the base member 26 from which the fixation keel 27 extends and the provision of a coracoid notch 29 on such side of the base member 26 requires removal of the natural glenoid surface from the scapula as is readily seen in FIG. 1 of such patent.

Similarly, U.S. Pat. No. 4,964,685 (incorporated herein by reference) requires resecting the glenoid cavity to provide a flat resected surface against which the flat medial surface of the glenoid component rests. The bone of the scapula 130 is resected in an amount substantially equal to the height of the side walls 40 of the prosthesis to provide a flat resected surface 146. Additionally, two peg holes 142, 143 are drilled into the tissue 139 of the scapula 130 with the result that significant amounts of bone tissue are removed from the patient in preparation for implantation of the glenoid component.

U.S. Pat. No. 4,261,062 shows a natural shoulder joint prosthesis having a glenoid component with an elliptical configuration and a tapered keel 36 having a series of transversely extending ribs 40, 42, and 44.

U.S. Pat. No. 4,865,605 discloses a modular shoulder prosthesis having a glenoid component 30 with a stem 37 extending from a flat surface of the base 33 for implanting in a prepared cavity of the scapula.

DISCLOSURE OF THE INVENTION

The present invention is directed to a glenoid component which is designed to permit implantation in the scapula with a minimal amount of bone removal required in preparation of the scapula for implantation of the glenoid component. The present invention is also directed to a method for implanting such glenoid component for precise placement in the scapula and precise drilling and reaming of the scapula utilizing a tapered cannulated reamer and a guide wire which is preliminarily affixed in a centralized desired location of the scapula and to apparatus useful in performing such method.

The glenoid component itself includes a (1) body portion having (i) a smooth concave lateral articulating surface facing away from the scapula adapted to be engaged by a convex surface of a humeral component and (ii) an opposing surface on the medial side intended to be positioned within a cavity reamed in the scapula and (2) a stem extending from said medial side along an axis. The surface of such medial side includes a tapered portion which extends outwardly from the stem and tapers away from the stem as it extends outwardly from the axis with such tapered portion terminating in a curved line which is substantially circular in configuration. Under one embodiment, the body portion extends to an edge having a circular configuration while, under a second embodiment, the body portion has an edge defining a non-circular configuration such as an oval or elongated configuration or a configuration which may be characterized as rectangular with slightly rounded ends. Under the second embodiment, the medial side of the prosthesis has extensions beyond the circular line of termination of the tapered surface portion, which extensions are disposed at an angle with respect to the axis which is different from the angle at which the tapered surface is disposed. The glenoid component of the second embodiment is implanted in a prepared cavity of the scapula which conforms generally to the stem and tapered surface only with the result that those portions of the glenoid component forming the extensions beyond the circular line of termination will lie on proximal portions of the scapula which have been prepared with minimal cutting.

In the method of implanting the glenoid component, the first step after exposing the glenoid cavity is to determine the appropriate size of component to be used. This is done by placing a series of circular sizers having varying diameters over the glenoid cavity to determine the proper diameter to which the scapula should be reamed at the surface defining the glenoid cavity and the proper size of glenoid component. Using a combined sizer/guide having a central hole and passageway formed therein to determine the correct location and attitude, a hole is drilled a few millimeters into the scapula through the glenoid surface using a combined guide wire/drill. The guide wire/drill is calibrated in order to readily determine the depth of drilling and is attached to a chuck if a power drill is used or a T-handle or the like if the drilling is manual. The guide wire/drill should be drilled into the scapula substantially perpendicular to the glenoid surface. Thereafter, the combined sizer/guide is removed and a cannulated reamer is positioned over the guide wire/drill to ream the scapula to the proper shape and depth forming a cavity having a circular cross-sectional configuration in a plane normal to the axis defined by the guide wire.

BEST MODE OF CARRYING OUT INVENTION

Figure 1:
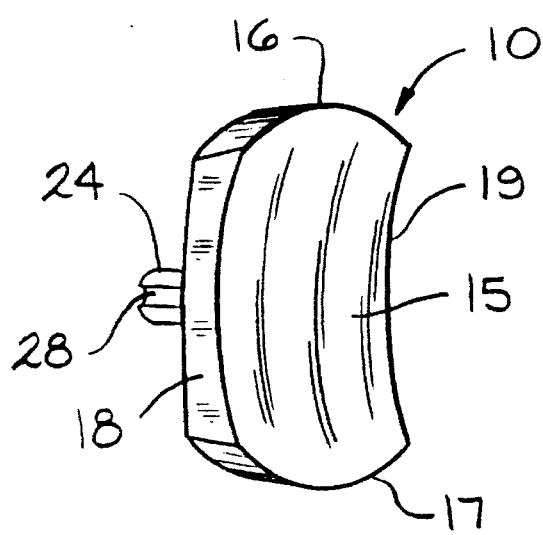
FIG. 1 is a perspective view of the glenoid component of the present invention as viewed generally from the lateral articulating surface intended to be engaged by the humeral component.

Referring now to FIGS. 1–5, there is provided a glenoid component 10 which is intended to be implanted in the scapula S as part of total shoulder replacement arthroplasty. The glenoid component 10 replaces the natural glenoid cavity G and provides a bearing surface against which the head 11 of a humeral component 12 may ride. As may be seen in FIG. 4, the humeral component 12 includes a stem 13 which is implanted in a prepared medullary canal of the humerus H. The head 11 is secured to that portion of the stem 13 extending from the proximal end of the humerus.

The glenoid component 10 of the present invention includes a concave lateral articulating surface 15 against which the head 11 of the humeral component 12 moves. The glenoid component 10 is manufactured of a suitable non-metallic material such as high density high molecular weight polyethylene or similar compatible material with the lateral articulating surface 15 being smoothly contoured, preferably in a spherical concavity which has a radius of curvature significantly larger than the radius of curvature of the head 11 to allow substantially free sliding and rotational movement of the head 11 on the articulating surface 15.

In the embodiment shown in FIGS. 1, 2, 4 and 5, the glenoid component 10 includes a body portion bounded by a superior edge 16, an oppositely disposed inferior edge 17, a posterior edge 18 and an oppositely disposed anterior edge 19. Each of posterior edge 18 and anterior edge 19 extends between the superior edge 16 and the inferior edge 17. The respective edges 16, 17, 18 and 19 define the perimeter of the lateral articulating surface 15. As may be seen in FIGS. 2 and 4, the glenoid component 10 has a medial side 20 which includes a central tapered portion 21 and extension portions 22 and is adapted to be implanted in a prepared cavity 23 of the scapula S, being retained therein with bone cement 14. The extension portions 22 extend, respectively, to the superior edge 16 and the inferior edge 17. The central tapered portion 21 has a central post or stem 24 extending therefrom along an axis A. The central tapered portion 21 is preferably conical in shape and extends from the stem 24 outwardly and toward the lateral articulating surface 15 and terminates in a circular line of juncture 25. The extension portions 22 are outside of the line of juncture. Preferably, the circular line of juncture meets the posterior edge 18 and the anterior edge 19. Thus, the construction of the glenoid component 10 is such that, by virtue of its taper in the central tapered portion 21, it is significantly thicker in the area adjacent the post 24 than in areas outwardly therefrom. Although it is preferred that the central tapered portion 21 follows a straight line path along its surface as viewed in FIG. 4, it could follow a curve path, either concave or convex.

Figure 2:
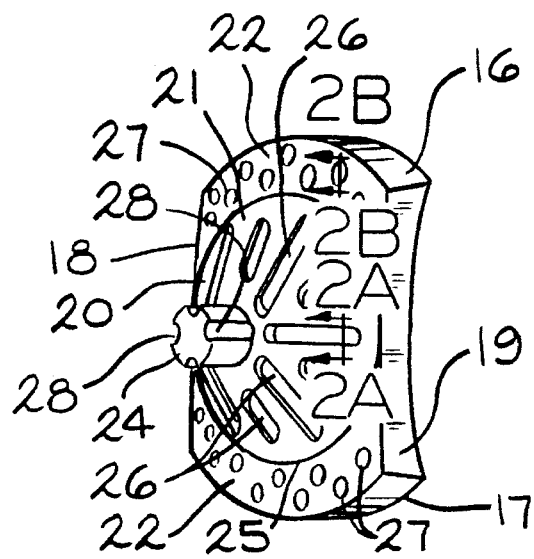
FIG. 2 is a perspective view of such glenoid component as viewed generally from the medial side intended to be implanted in a prepared cavity of the scapula.
Figure 2A:
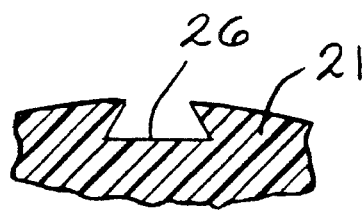
FIG. 2A is a sectional view taken through line 2A—2A of FIG. 2.
Figure 2B:
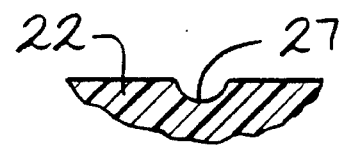
FIG. 2B is a sectional view taken through line 2B—2B of FIG. 2.
Figure 3:
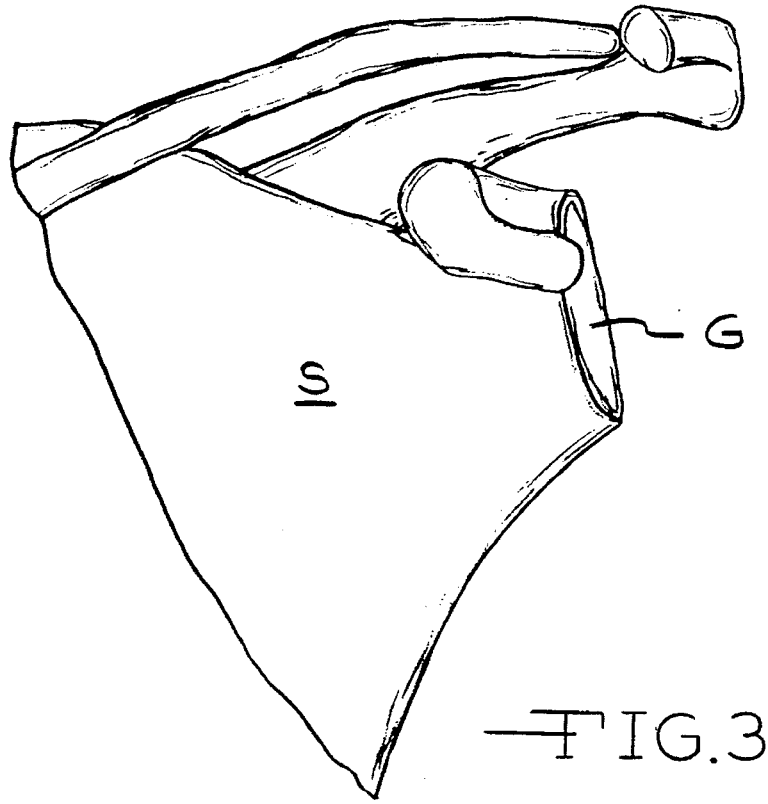
FIG. 3 is a perspective view showing a scapula in which the glenoid component of the present invention is to be implanted.

The central tapered portion 21 is preferably roughened or textured and is provided with a series of elongated grooves 26 in multiple locations for receiving bone cement 14 to assist in the cement augmentation and retention of the glenoid component 10. Preferably, the elongated recesses 26 have one or more portions with an undercut or a reverse taper to assist with cement augmentation. (See FIG. 2A). Additionally, the extension portions 22 are roughened or textured and are provided with a series of depressions 27 which will receive bone cement 14 and assist in the cement augmentation.

The stem or post 24 is provided with a series of longitudinal slots 28 which also function to provide cement augmentation and assist in the prevention of rotation of the glenoid component 10 in the prepared cavity 23.

The extension portions 22 are disposed at an angle with respect to the axis A which is substantially the same as the angle of the natural glenoid surface G in that area such that minimal cutting or surface preparation of the natural glenoid surface G in the areas to be overlied by such extension portions 22 will be required. It is desirable, however, to drill small depressions 29 in that portion of the natural glenoid surface G to further assist in cement augmentation.

Thus, in preparing the scapula S to receive the glenoid component 10 only that portion of the scapula S lying within a circle of the size defined by the line of juncture 25 will need to be reamed. As will be appreciated, this reduces to a minimum the amount of bone tissue which must be removed from the scapula S in order to implant the glenoid component 10 therein. As previously mentioned, it is desirable that as little bone as possible be removed in preparing the scapula S to receive the glenoid component 10 thereby reducing the chances of fracture or damage to the adjacent vital structures and allows secure fixation of the glenoid component.

Referring now to FIGS. 6–14, there will now be described a method for preparing a cavity in the scapula S for receiving the glenoid component 10 of the present invention and apparatus to be used therewith.

FIGS. 6–9, 12 and 13 show a combined sizer/guide 30. The combined sizer/guide 30 includes a tubular guide member 31 having a central passageway 32 extending therethrough and a first sizer 33 mounted on one end and a second sizer 34 mounted on the other end. Extending outwardly from each of the first sizer 33 and second sizer 34 are a plurality of pointed members 35. The sizer 33 has an exterior wall surface 33A defining a circle of predetermined diameter, for example 22 millimeters and the second sizer 34 has an exterior wall surface 34A defining a circle having a different diameter, for example 25 millimeters. Among the purposes of the sizers 33 and 34 is to assist the surgeon in measuring the size of the natural glenoid cavity G in order to determine what size and type of glenoid component is best suited for the particular patient undergoing surgery. As will be appreciated, additional combined sizers/guides with differing sizes of diameters may be provided to assist the surgeon; however, in order to reduce the number of combined sizers/guides required to be maintained by the surgeon or hospital, it is desirable that each of the sizers 33, 34 on any combined sizer/guide 30 be of different sizes.

Figure 12:
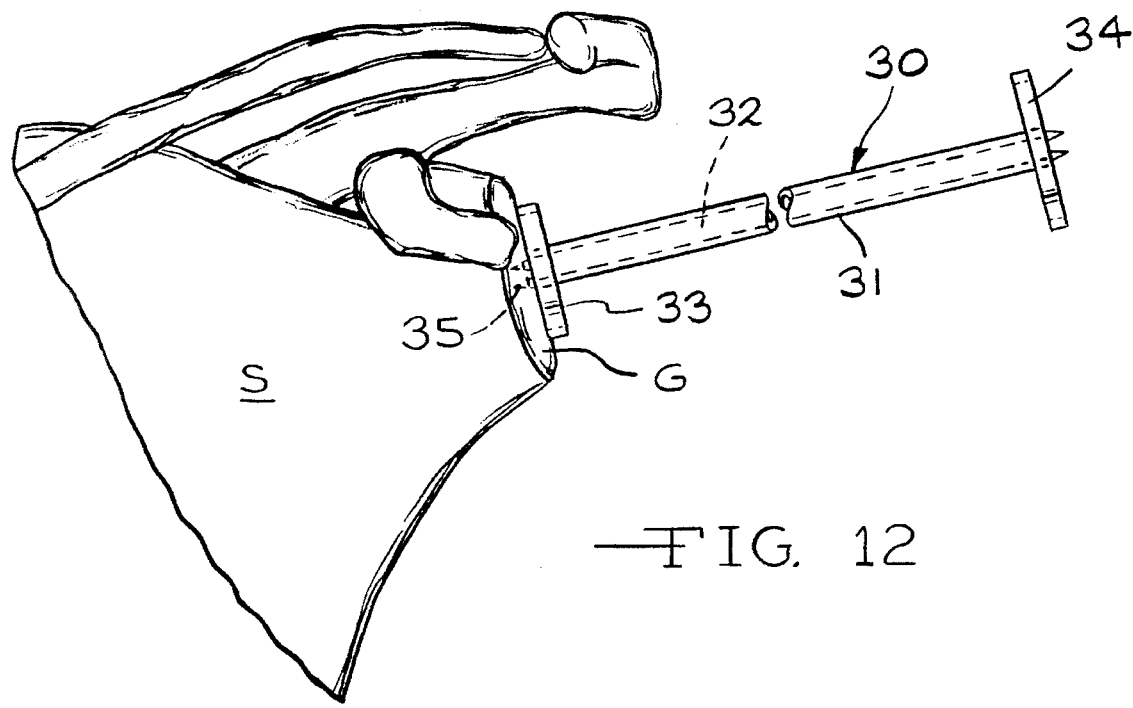
FIG. 12 is a schematic view showing the initial positioning of the sizer/guide.
Figure 13:
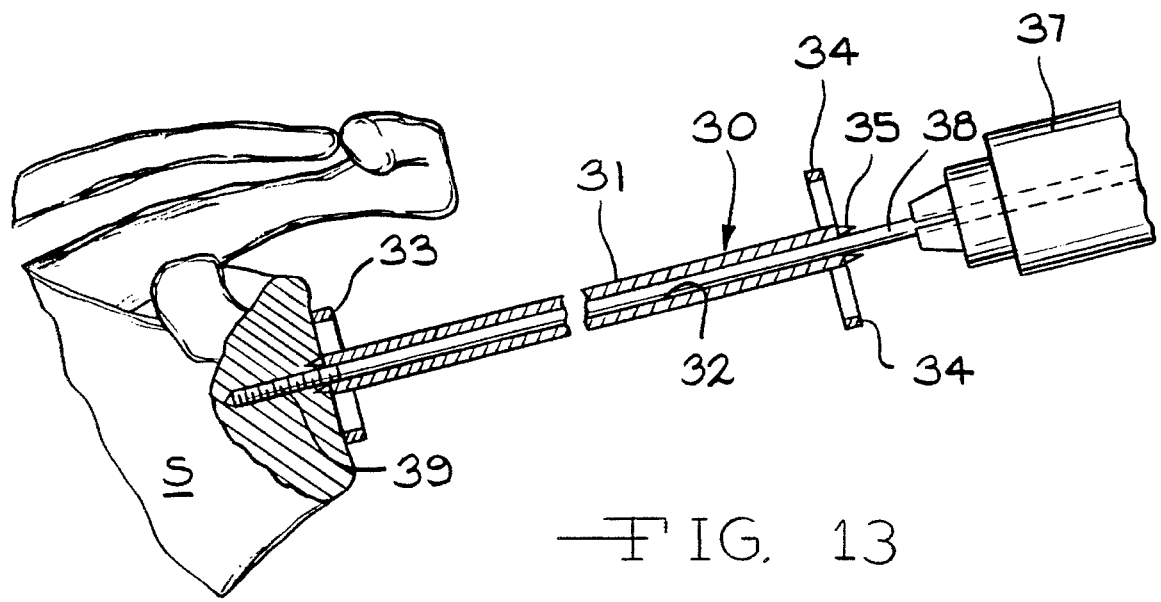
FIG. 13 is a view showing the use of the sizer/guide as a guide in obtaining proper depth of the drill.

In preparing the cavity 23 in the scapula S to receive the glenoid component 10, the surgeon will initially position the combined sizer/guide 30 with one of the sizers 33 or 34 in loose contact with the glenoid cavity G of the scapula S and, through trial and error, determine which size of sizer is appropriate for the particular patient. As shown in FIG. 12, the smaller first sizer 33 was determined to be appropriate. With the combined sizer/guide 30 appropriately centrally positioned in the glenoid cavity G, the combined sizer/guide 30 is struck with a hammer to drive the point members 35 into the bone of the scapula S in order to fix the combined sizer/guide 30 in position.

A combined guide wire/drill bit 38 is inserted through the passageway 32 and, using a drill 37 is drilled a distance of about 15–30 millimeters into the scapula S. If desired, the guide wire/drill bit 38 may be manually rotated in place of using a drill 37. The combined guide wire/drill bit 38 is calibrated as at 39 in order to ascertain the proper depth. The drill 37 is removed from the combined guide wire/drill 38 and the combined sizer/guide 30 is then removed from the guide wire/drill 38 while leaving the guide wire/drill 38 in the newly drilled portion of the scapula S.

Figure 10:
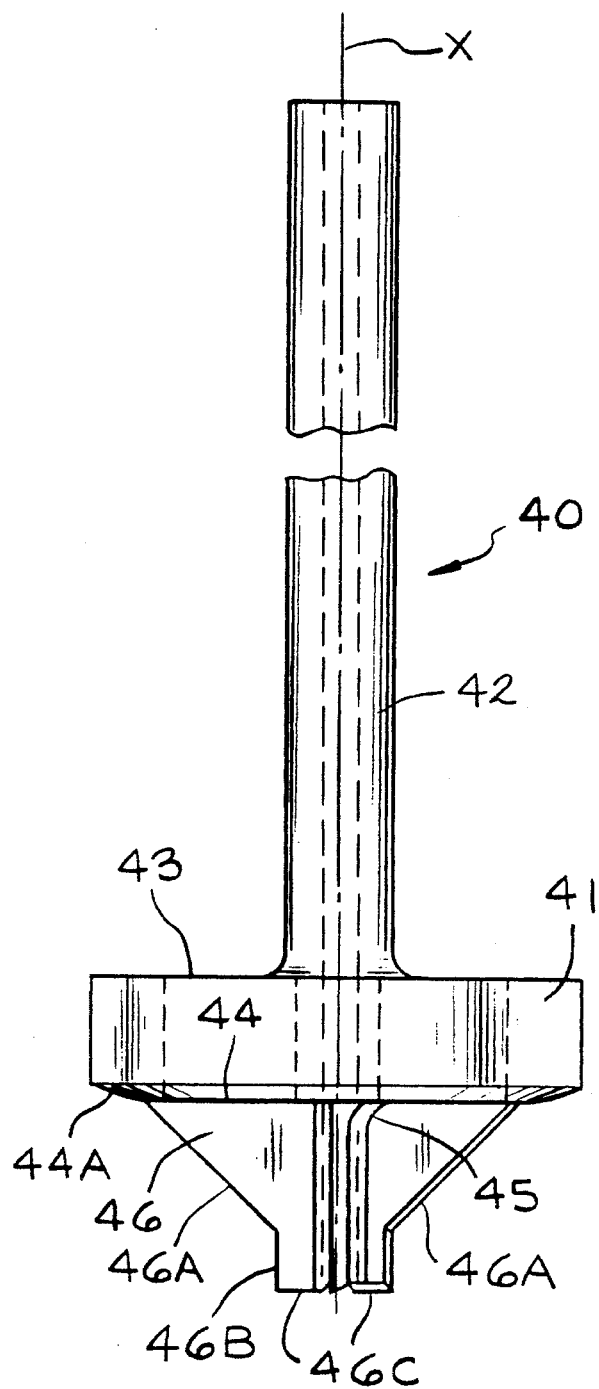
FIG. 10 is an elevational view of a cannulated reamer for use in forming a cavity in which the glenoid component is to be positioned.
Figure 11:
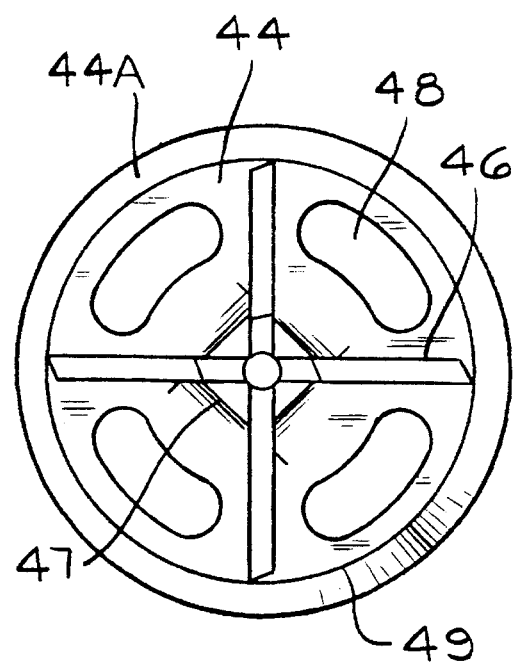
FIG. 11 is a plan view looking toward the cutting face of the reamer of FIG. 10.
Figure 14:
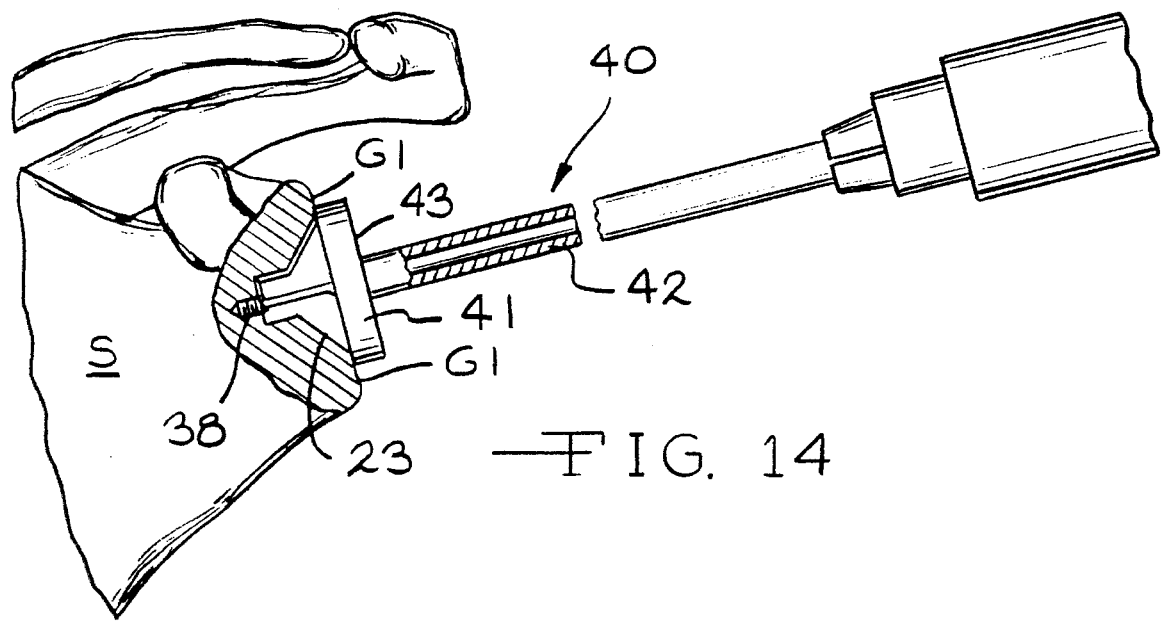
FIG. 14 is a schematic view partially in section showing the reaming step.
Figure 15:
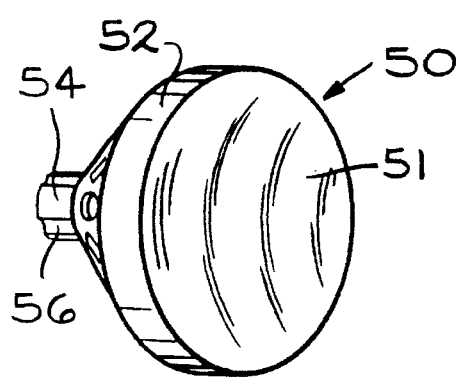
FIG. 15 is a perspective view of a modified embodiment as viewed from the concave lateral articulating surface.
Figure 16:
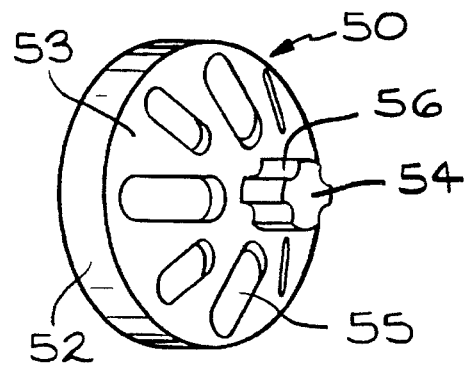
FIG. 16 is a view of the glenoid component of FIG. 15 as viewed from the tapered medial side.
Figure 17:
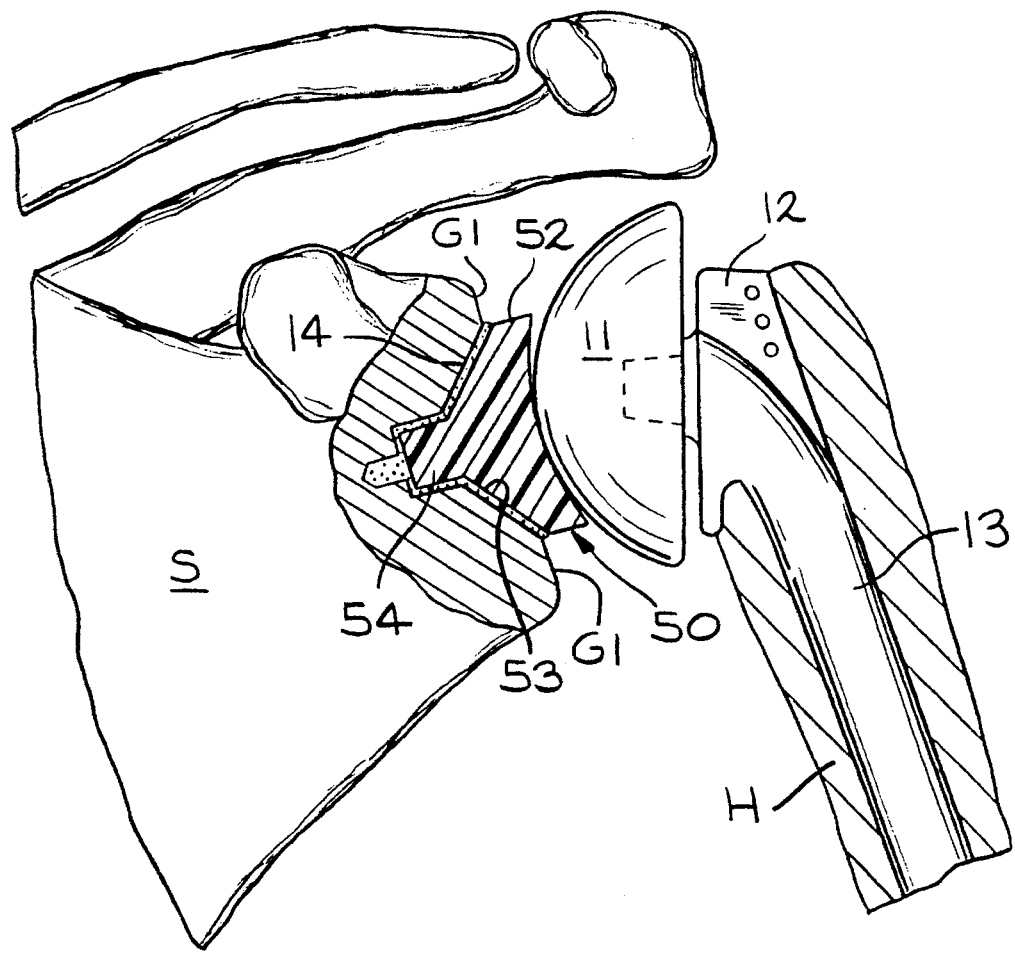
FIG. 17 is a sectional view showing the glenoid component of FIGS. 15 and 16 implanted in the prepared cavity of the scapula.
Figure 18:
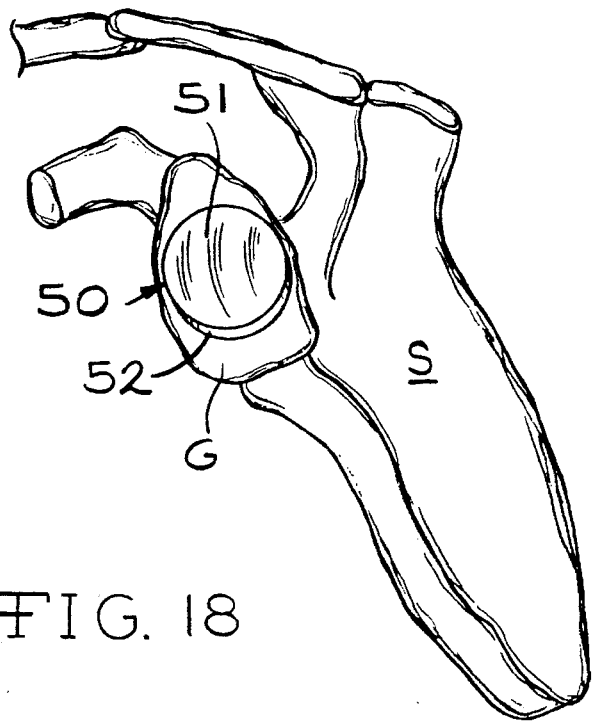
FIG. 18 is a view showing the glenoid component of FIGS. 15 and 16 fully implanted in the scapula looking toward the lateral articulating surface.

Referring to FIGS. 10, 11 and 14, there is then provided a reamer 40 having a head 41 mounted on the end of a cannulated stem 42 extending along on axis X. The head 41 has an upper surface 43 and a lower surface 44. A cutting assembly 45 extends downwardly from the lower surface 44 of the head and includes a plurality of cutting blades 46 extending outwardly from a central housing 47 and downwardly from the lower surface 44 of the head 41. Each of the cutting blades 46 has a substantially identical configuration which is tailored to form a cavity of a size and shape suitable for receiving the central tapered portion 21 and stem 24 of the glenoid component 10 or other tapered glenoid component such as that to be hereinafter described. As shown in FIGS. 10 and 11, four cutting blades 46 are provided. However, there could be a greater or fewer number of such cutting blades. Each of the cutting blades 46 has a first cutting edge 46A which tapers downwardly from the lower surface 44 and inwardly toward the axis X at an angle substantially equal to the angle of the central tapered portion 21 of the glenoid component 10 relative to the axis A. The distance from the point of juncture between the first cutting edge 46A and the lower surface 44 to the axis X is about one-half of the diameter of the circle defined by the line of juncture 25. Thus, the diameter of cavity 23 reamed in the scapula S at the glenoid surface G will be substantially the same as the diameter of the line of juncture 25 for the proper size of glenoid component 10. Each of the cutting blades 46 also has a second cutting edge 46B substantially parallel to the axis X and a third cutting edge 46C extending radially inwardly from the second cutting edge 46B and joined to the housing 47. The second cutting edge 46B and third cutting edge 46C will form a cylindrical cavity portion sufficiently large to receive the stem 24 of the glenoid component 10.

As can be seen in FIGS. 10 and 11, the cutting blades 46 do not extend outwardly to the outer periphery of the head 41. Thus, the first cutting edge 46A is joined to the lower surface 44 at a substantial distance, on the order of one to two millimeters, inwardly from the outer periphery of the head 41. The lower surface 44 has a circular line of juncture 49 passing through each of the points of juncture between each of the first cutting edges 46A and the lower surface 44. The outer peripheral portion 44A of the lower surface 44 between the line of juncture 49 and the edge of the head 41 is convexly curved to approximately match the corresponding concavity of the natural glenoid cavity G. This construction permits the lower surface peripheral portion 44A to contact the natural glenoid G and function as a stop for determining the proper depth of the cavity and insure against inadvertent reaming of the scapula S to an excessive depth.

The head has a plurality of openings 48 to provide a means for expelling bone chips and other debris as the reaming operation takes place. If desired, the openings 48 may be inclined to facilitate propelling of debris therethrough. Preferably there will be the same number of openings 48 as there are cutting blades 46.

Referring now to FIG. 14, with the guide wire/drill 38 remaining in position in the scapula S, the reamer 40 is positioned such that the guide wire/drill 38 extends through the cannulated stem 42. The reamer 40 is then rotated by suitable power means or by hand to ream a cavity 23 having a size and configuration such as shown in FIG. 14. Following such reaming, the reamer 40 and the guide wire/drill 38 are removed leaving a cavity 23 which is substantially wholly contained within the glenoid cavity G. Thereafter, if it is desired to use a glenoid component 10 of the type shown in FIGS. 1, 2 and 4, the outer margins G1 of the glenoid cavity G which was not cut by the reamer is roughened and, if desired, has small depressions 29 formed therein about the size of the depressions 27 of the glenoid component 10 to assist in cement augmentation.

Thereafter, a suitable bone cement 14 such as polymethylmethacrylate (PMMA) or a compatible fixation material is placed in the reamed cavity 23 and in the roughened outer portions G1 and depressions 29 and the glenoid component 10 is positioned therein.

Figure 4:
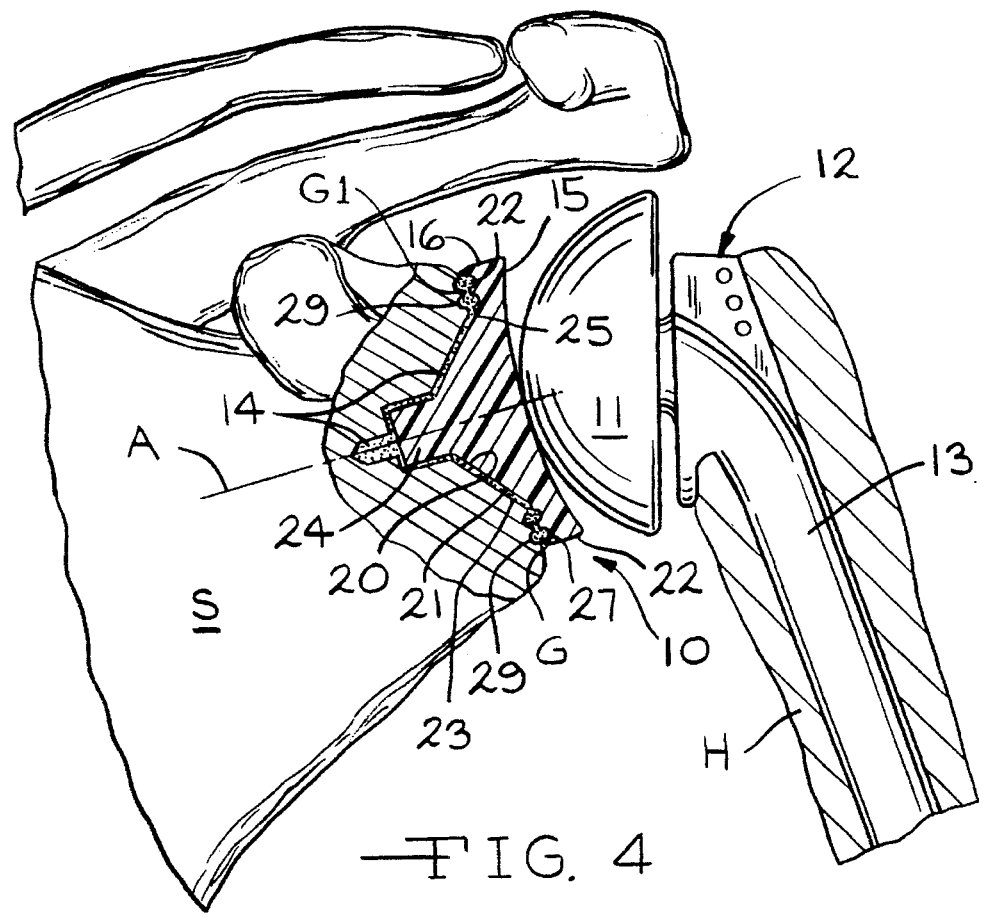
FIG. 4 is a sectional view showing the glenoid component of FIGS. 1 and 2 fully implanted in the scapula and engaged by a humeral component.
Figure 5:
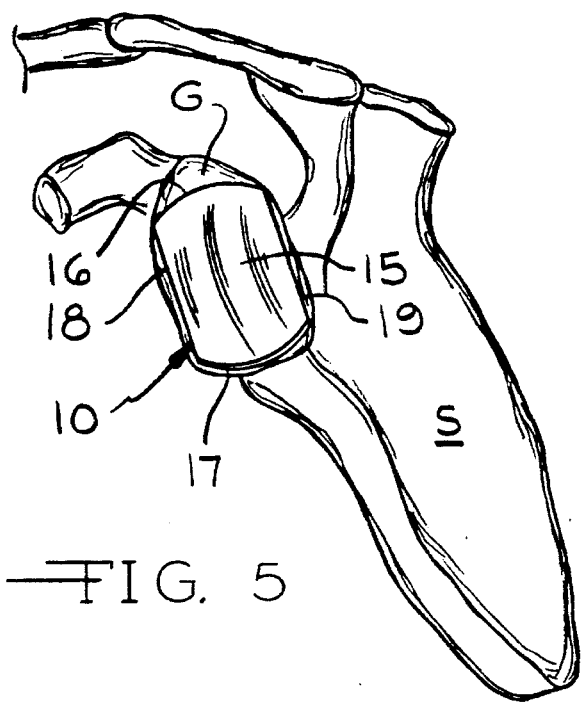
FIG. 5 is a view showing the glenoid component of FIGS. 1 and 2 fully implanted in the scapula looking toward the lateral articulating surface.
Figure 6:
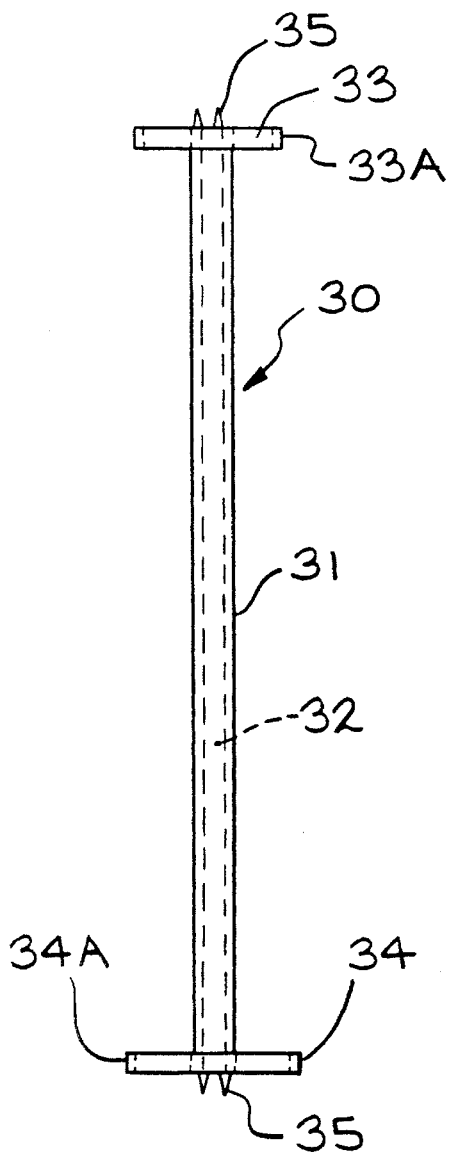
FIG. 6 is an elevational view of a sizer/guide for use (1) in determining the correct size of glenoid component to be used and (2) in positioning the guide wire.
Figure 7:
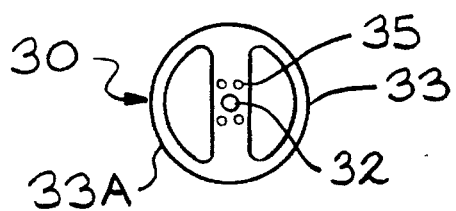
FIGS. 7 and 8 are top and bottom plan views of the sizer/guide.
Figure 8:
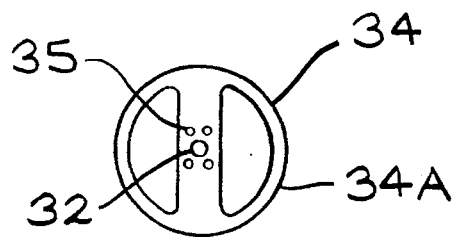
Figure 9:
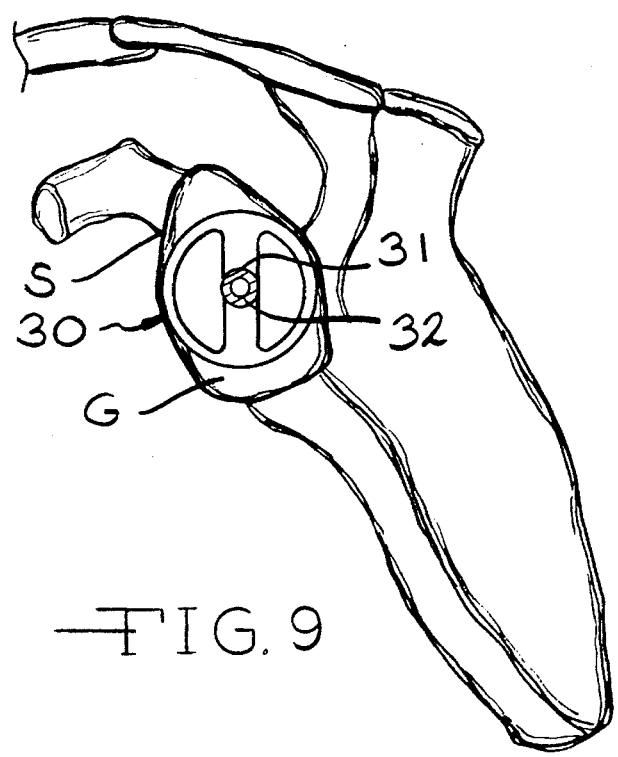
FIG. 9 is a view showing the sizer/guide in position facing the glenoid cavity of a scapula.

As can be appreciated, the reaming may be contained wholly within the boundary of the glenoid cavity G and therefore does not destroy the margin of the glenoid surface. Additionally, as can be seen in FIGS. 4 and 5, there preferably is no overhang of the glenoid component 10 beyond the margin of the natural glenoid cavity.

Referring now to FIGS. 15–18, there is shown a modified glenoid component 50 having a lateral articulating surface 51 having a concave spherical surface encircled by a circular edge 52. The circular edge 52 has a thickness in the range of 1 to 3 mm.

The modified glenoid component 10 has a medial side 53 which is tapered similar to the central tapered portion 21 of the medial side 20 of the glenoid component 10 of the previous embodiment. The medial side 53 has a central post or stem 54 extending from a central portion thereof along an axis similar to the extension of stem 24 along axis A of glenoid component 10. A plurality of grooves 55 are formed in the medial side 53 to assist in cement augmentation. The areas of the medial side 53 between the grooves 55 are roughened or textured to assist in cement augmentation. As in the previous embodiment the post/stem 54 may be provided with a series of longitudinal grooves 56 to assist in preventing rotation of the glenoid component 50 following implantation.

Figure 19:
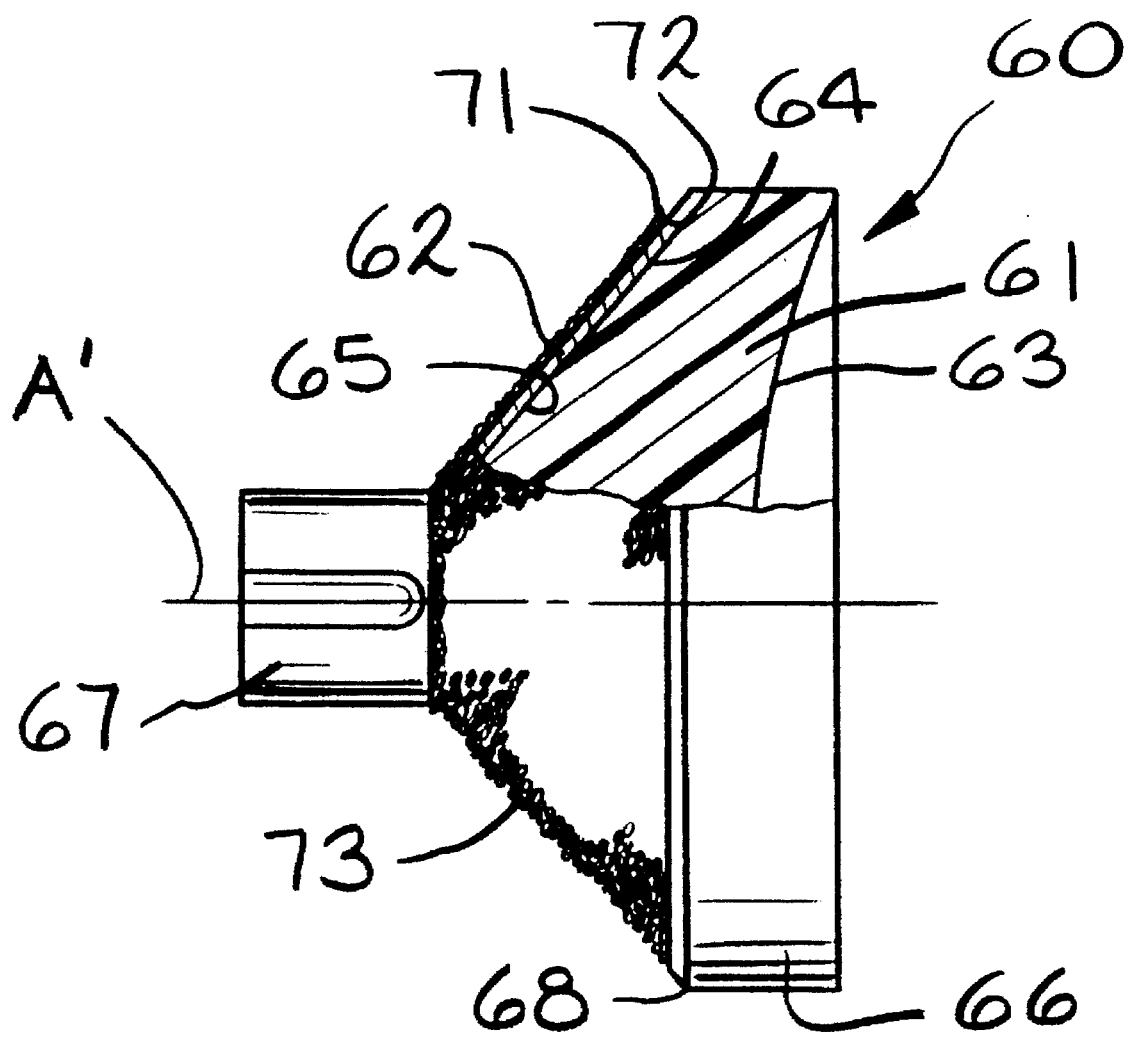
FIG. 19 is a side view partly in section of a further embodiment intended for use without bone cement as viewed from the medial side.

Referring now to FIG. 19, there is shown a further embodiment of glenoid component 60 which is intended to be implanted in a prepared cavity of the scapula without the use of bone cement. The glenoid component 60 includes a plastic member 61 and a metal member 62. The plastic member 61 includes a concave lateral articulating surface 63 which is smoothly contoured and an opposed medial side 64 which includes a central tapered portion 65 and a central post or stem 67 extending therefrom along an axis A'. An edge 66 having a circular cross-sectional configuration extends between the lateral articulating surface 63 and the medial side 64. As in the embodiment shown in FIGS. 1, 2, 4 and 5, the central tapered portion 65 of the glenoid component 60 of the present embodiment extends from the stem 67 outwardly and tapers toward the lateral articulating surface 63 and terminates in a circular line of juncture 68. Since the glenoid component 60 of the present invention is intended for use without bone cement, the central tapered portion 65 of the medial side 64 is generally smooth.

The metal member 62 is secured to the medial side 64 in confronting relationship with the central tapered portion 65 and is retained thereagainst by means of a friction fit with an edge 71 of the metal member 62 retained in a recess 72 in the central tapered portion 65 near the edge 66.

The metal member includes a series of beads 73 affixed thereto by sintering or other means well known in the art of joint prosthesis manufacture. The beads 73 form a porous surface intended to receive bone ingrowth for retaining the glenoid component 60 in the prepared cavity without cement. Porous metal surfaces having structures of the types produced by Astro Met, Inc., Cincinnati, Ohio, and marketed under the name "Astro Met" may be used as a surface for promoting bone ingrowth. U.S. Pat. No. 4,164,794 discloses a prosthetic device having sintered porous coating of selected bio-engineered thermoplastics which could also be used for such porous surface in lieu of the metal member 62.

Although the glenoid component 60 has been shown as having an edge 66 with a circular cross-sectional configuration and no extensions, it should be appreciated that it is within the contemplation of the present embodiment that a prosthesis having a central tapered portion extending to a circular line of juncture and extension portions outwardly of said line of juncture and with porous ingrowth material on the medial side, including the extension portions, could also be utilized.

Many other modifications will become readily apparent to those skilled in the art. Accordingly, the scope of the present invention should be determined only by the scope of the claims appended hereto.

I claim:

1. A glenoid component of a shoulder prosthesis comprising:
   (a) a stem extending along an axis from a free end to a second end; and
   (b) a body extending from said second end, said body including,
      (i) a bone engaging medial surface extending from said stem away from said axis and terminating at a curved line approximating a circle;
      (ii) a lateral articulating surface spaced from said medial surface and defining a smooth cavity; and
      (iii) a peripheral edge extending between said medial surface and said lateral articulating surface,
   said medial surface tapering toward said lateral articulating surface in a direction outwardly from said stem, said medial surface having a pair of extensions beyond said curved line, said edge having a non-circular configuration and said extensions being disposed at an angle relative to said tapering medial surface within said curved line.

2. The glenoid component of claim 1, wherein said tapered portion has a plurality of grooves formed therein.

3. The glenoid component of claim 2, wherein said grooves include one or more portions having a reverse taper defining an undercut.

4. The glenoid component of claim 2, wherein said extensions have a plurality of depressions formed therein.

5. The glenoid component of claim 1, wherein said stem has a plurality of grooves extending in a direction parallel to said central axis.

6. The glenoid component of claim 1, wherein said medial surface includes areas adapted for receiving bone in-growth.

7. The glenoid component of claim 1, further including a metal member having a first side contacting said medial surface and a second side with a porous surface for receiving bone in-growth.

8. A glenoid component comprising:
   (a) a body having a concave lateral articulating surface and an opposing bone engaging medial surface, said medial surface including (i) a substantially circular central portion extending outwardly from a central axis and tapering toward said lateral articulating surface from an area of greater thickness of said body in the vicinity of said central axis to an area of lesser thickness outwardly from said central axis, said central portion terminating at a line defining, at least, a segment of a circle and (ii) a pair of extension portions disposed at an angle relative to said central portion;
   (b) a stem extending from said medial surface along said central axis; and
   (c) a peripheral edge having a non-circular configuration extending between said lateral articulating surface and said medial surface, said central portion terminating line being spaced from said edge in two opposing areas to define said pair of extension portions, said stem being positioned between said extension portions.

9. The glenoid component of claim 8, wherein said central portion has a plurality of grooves formed therein.

10. The glenoid component of claim 9, wherein said grooves include one or more portions having a reverse taper defining en undercut.

11. The glenoid component of claim 8, wherein said extensions have a plurality of depressions formed therein.

12. The glenoid component of claim 8, wherein said stem has a plurality of grooves extending in a direction parallel to said central axis.

13. The glenoid component of claim 8, wherein said medial surface includes areas adapted for receiving bone in-growth.

14. The glenoid component of claim 8, further including a metal member having a first side contacting said medial surface and a second side with a porous surface for receiving bone in-growth.

15. A glenoid component of a shoulder prosthesis comprising:
(a) a stem extending along an axis from a free end to a second end; and
(b) a body extending from said second end, said body including,
  (i) a bone engaging medial surface having (A) a substantially circular central portion extending from said stem away from said axis and terminating at a curved line approximating a circle and (B) two extension portions, said stem being positioned between said extension portions;
  (ii) a lateral articulating surface spaced from said medial surface and defining a smooth concavity; and
  (iii) a peripheral edge extending between said medial surface and said lateral articulating surface, said medial surface central portion tapering toward said lateral articulating surface in a direction outwardly from said stem and defining an angle relative to said extension portions.

* * * * *